US010634889B2

(12) United States Patent
Tamura et al.

(10) Patent No.: US 10,634,889 B2
(45) Date of Patent: Apr. 28, 2020

(54) MEDICAL OBSERVATION APPARATUS AND MEDICAL OBSERVATION SYSTEM

(71) Applicant: Sony Olympus Medical Solutions Inc., Tokyo (JP)

(72) Inventors: Shigeru Tamura, Tokyo (JP); Kenji Hirose, Tokyo (JP); Yoshiyuki Kamata, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 15/328,522

(22) PCT Filed: Aug. 13, 2015

(86) PCT No.: PCT/JP2015/072935
§ 371 (c)(1),
(2) Date: Jan. 24, 2017

(87) PCT Pub. No.: WO2016/027749
PCT Pub. Date: Feb. 25, 2016

(65) Prior Publication Data
US 2017/0212339 A1     Jul. 27, 2017

(30) Foreign Application Priority Data

Aug. 21, 2014  (JP) ................. 2014-168842

(51) Int. Cl.
*G02B 21/00* (2006.01)
*A61B 90/25* (2016.01)
(Continued)

(52) U.S. Cl.
CPC .......... *G02B 21/0012* (2013.01); *A61B 90/25* (2016.02); *G02B 7/001* (2013.01); *A61B 2090/373* (2016.02); *G02B 21/365* (2013.01)

(58) Field of Classification Search
CPC .. G02B 21/0012; G02B 7/001; G02B 21/365; A61B 90/25; A61B 2090/373
(Continued)

(56) References Cited

U.S. PATENT DOCUMENTS 5,667,186 A    9/1997 Luber et al.

FOREIGN PATENT DOCUMENTS

DE    10 2010 043 919 A1    5/2012
JP        2001-51204 A    2/2001
(Continued)

OTHER PUBLICATIONS

International Search Report dated Nov. 2, 2015 in PCT/JP2015/072935 filed Aug. 13, 2015.
(Continued)

*Primary Examiner* — On S Mung
(74) *Attorney, Agent, or Firm* — Xsensus LLP

(57) ABSTRACT

Provided are a medical observation apparatus and a medical observation system that are optimal in manipulability and favorable for downsizing and include: an observation unit including a microscope unit that is configured to collect light from an object to be observed via one end in a height direction of the microscope unit and capture a magnified image of a minute part of the object to be observed and has a columnar shape to be grasped by a user during movement, a center of gravity of which observation unit is located farther from the one end than a center in the height direction is; and a support unit supporting the observation unit in a rotationally movable manner around an axis passing through the center of gravity or a vicinity of the center of gravity and perpendicular to the height direction.

13 Claims, 6 Drawing Sheets

(51) Int. Cl.
  *G02B 7/00* (2006.01)
  *G02B 21/36* (2006.01)
  *A61B 90/00* (2016.01)

(58) Field of Classification Search
  USPC .......................................................... 348/79
  See application file for complete search history.

(56) References Cited

FOREIGN PATENT DOCUMENTS

| JP | 2001-051204 A | | 2/2001 |
|----|----|----|----|
| JP | 2005-13715 A | | 1/2005 |
| JP | 2005-43458 A | | 2/2005 |
| JP | 2005-43458 A | | 2/2005 |
| JP | 2005-043458 A | | 2/2005 |
| JP | 2005043458 A | * | 2/2005 |
| JP | 2005-87249 A | | 4/2005 |
| JP | 2005-087249 A | | 4/2005 |
| JP | 2005224367 A | * | 8/2005 |
| JP | 2006-14825 A | | 1/2006 |
| JP | 2006-305156 A | | 11/2006 |
| JP | 2009-273714 A | | 11/2009 |

OTHER PUBLICATIONS

Extended European Search Report dated Mar. 16, 2018 in Patent Application No. 15833815.2, 7 pages.
Office Action dated May 22, 2018 in Japanese Patent Application No. 2014-168842, 9 pages.
Chinese Office Action dated Nov. 2, 2018 in Chinese Application No. 2015800430248, with English Translation (15 pages).
Japanese Office Action dated Dec. 11, 2018 for Japanese Application No. 2014-168842, 5 pages.

* cited by examiner

MEDICAL OBSERVATION APPARATUS AND MEDICAL OBSERVATION SYSTEM

TECHNICAL FIELD

The present disclosure relates to a medical observation apparatus and a medical observation system with which a minute part of an object to be observed is observed.

BACKGROUND ART

Thus far, as a technology for, when performing an operation of a minute part of the brain, the heart, etc. of a patient that is an object to be observed, observing the minute part, a technology that images the minute part and displays the captured image on a monitor has been known.

For example, Patent Literature 1 discloses an observation system including an observation apparatus including an objective optical system, an imaging device that captures an optical image incident on the objective optical system, and a movement mechanism that holds the observation apparatus and the imaging device and causes them to work together.

Further, Patent Literature 2 discloses a medical observation apparatus including a lens unit in a C-shaped configuration that includes an objective optical system, an imaging optical system, and a magnification changing optical system provided between the two optical systems and in which the magnification changing optical system is configured as a bending optical system and a support means that supports the lens unit movably.

CITATION LIST

Patent Literature

Patent Literature 1: JP 2005-13715A
Patent Literature 2: JP 2006-14825A

DISCLOSURE OF INVENTION

Technical Problem

For the medical observation apparatus, not only the demand for easier manipulation but also the demand to downsize the apparatus in order to ensure the visual field of an operator who is the user and save space is becoming stronger. However, in Patent Literatures 1 and 2 described above, the mechanism that moves a tip portion or a lens unit having the functions of observation and imaging is configured using a link mechanism or the like, and hence the structure is unavoidably complicated and increased in scale; and it is hard to say that the manipulability of the tip portion or the lens unit is good. Further, in the case of Patent Literature 2, also the configuration of the lens unit itself constitutes a hindrance to downsizing.

The present disclosure has been made in view of the foregoing, and an object of the present disclosure is to provide a medical observation apparatus and a medical observation system that are optimal in manipulability and favorable for downsizing.

Solution to Problem

In order to solve the above problem and achieve the object, a medical observation apparatus according to the present disclosure includes: an observation unit including a microscope unit that is configured to collect light from an object to be observed via one end in a height direction of the microscope unit and capture a magnified image of a minute part of the object to be observed and has a columnar shape to be grasped by a user during movement, a center of gravity of which observation unit is located farther from the one end than a center in the height direction is; and a support unit supporting the observation unit in a rotationally movable manner around an axis passing through the center of gravity or a vicinity of the center of gravity and perpendicular to the height direction.

In the medical observation apparatus, in the observation unit, a distance between the center of gravity and the one end may be larger than ½ of a height of the observation unit and not more than ⅔ of the height of the observation unit.

In the medical observation apparatus, the observation unit may further include a first joint unit holding the microscope unit in a rotationally movable manner around a first axis along the height direction, and a first arm unit holding, in its tip portion, the first joint unit and being held in its root end portion by the support unit in a rotationally movable manner around a second axis that is an axis perpendicular to the height direction and orthogonal to the first axis, and the center of gravity may be located at a point of intersection of the first axis and the second axis or is located nearer to the one end than the point of intersection is.

In the medical observation apparatus, in the first arm unit, a specific gravity of a first portion located on the one end side with respect to a plane passing through the second axis and orthogonal to the first axis may be smaller than a specific gravity of a second portion located on an opposite side to the first portion with respect to the plane.

In the medical observation apparatus, the observation unit may further include an input unit that is provided on a side surface of the microscope unit, is located nearer to the one end than the center of gravity is, and is configured to accept an input of an operation instruction to the microscope unit.

In the medical observation apparatus, the support unit may include at least one set composed of two arm units and a joint unit linking one of the two arm units to the other in a rotationally movable manner.

A medical observation system according to the present disclosure includes: the medical observation apparatus described above; a control device configured to perform signal processing on an imaging signal outputted by the medical observation apparatus to create image data for display; and a display device configured to display an image corresponding to image data created by the control device.

Advantageous Effects of Invention

According to the present disclosure, an observation unit including a microscope unit that collects light from an object to be observed via one end in the height direction of the microscope unit and captures a magnified image of a minute part of the object to be observed and that has a columnar shape to be grasped by the user during movement, the center of gravity of which observation unit is located farther from the one end than the center in the height direction is, and a support unit that supports the observation unit in a rotationally movable manner around an axis that passes through the center of gravity or the vicinity of the center of gravity and is perpendicular to the height direction are provided, and therefore a portion that the user grasps can be sufficiently ensured without increasing the size of the observation unit. Thus, a medical observation apparatus and a medical observation system that are optimal in manipulability and favorable for downsizing can be provided.

MODE(S) FOR CARRYING OUT THE INVENTION

Figure 1:
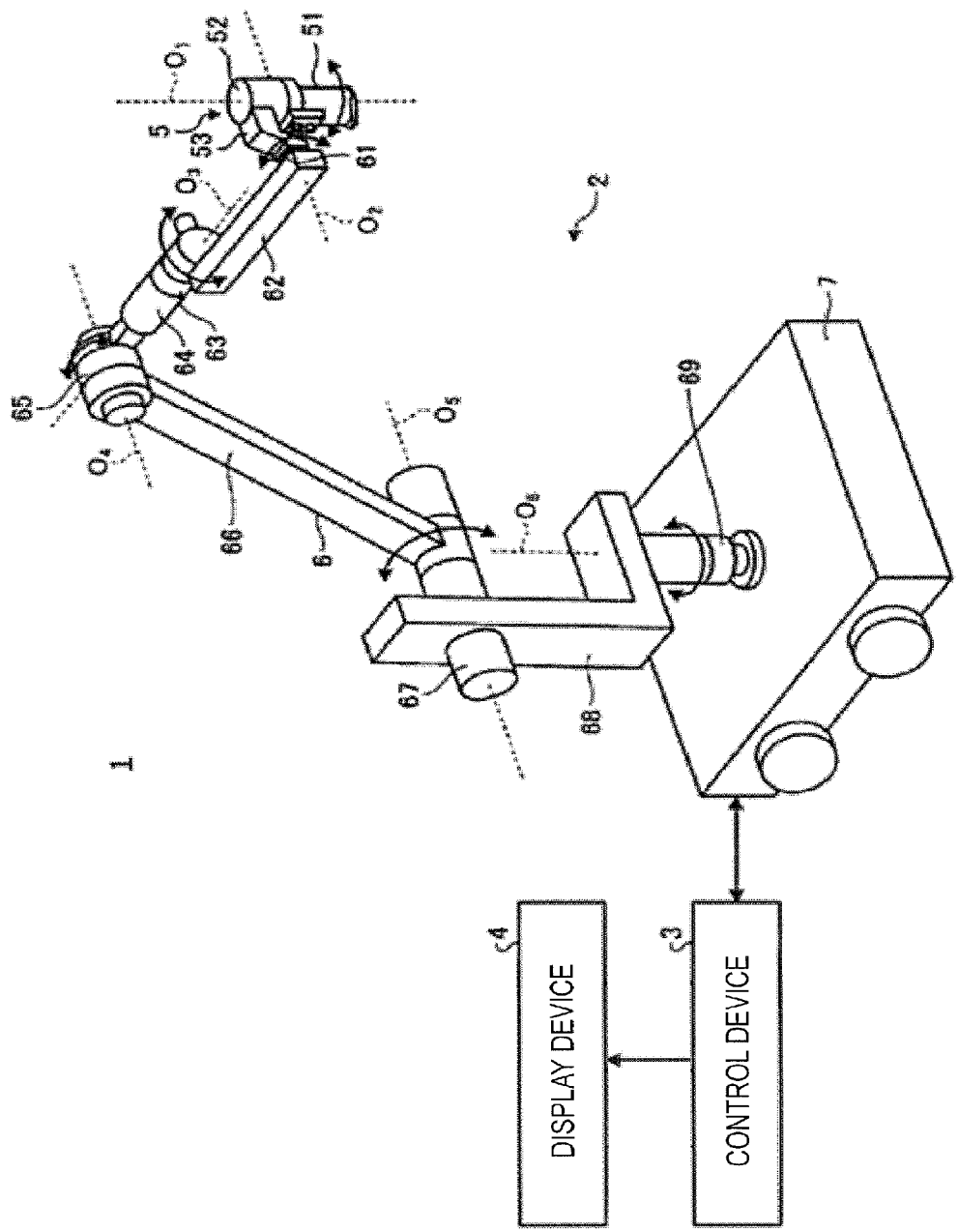
FIG. 1 is a perspective view showing an external configuration of a medical observation system according to Embodiment 1 of the present disclosure.

Hereinbelow, embodiments of the present disclosure (hereinafter, referred to as "embodiments") are described with reference to the appended drawings. The drawings are only schematic ones, and portions for which the relationships between dimensions and the proportions are different among drawings may be included in the drawings.
(Embodiment 1)

FIG. 1 is a diagram showing the configuration of a medical observation system according to Embodiment 1 of the present disclosure. A medical observation system 1 shown in the drawing includes a medical observation apparatus (hereinafter, referred to as an observation apparatus) 2 having a function as a microscope that images a minute structure of an object to be observed with magnification, a control device 3 that comprehensively controls the operation of the medical observation system 1, and a display device 4 that displays an image captured by the observation apparatus 2.

The observation apparatus 2 includes an observation unit 5 with which a minute part of an object to be observed is observed, a support unit 6 that is connected to a root end portion of the observation unit 5 and supports the observation unit 5 in a rotationally movable manner, and a base unit 7 that holds a root end portion of the support unit 6 in a rotationally movable manner and is capable of moving on the floor surface.

Figure 2:
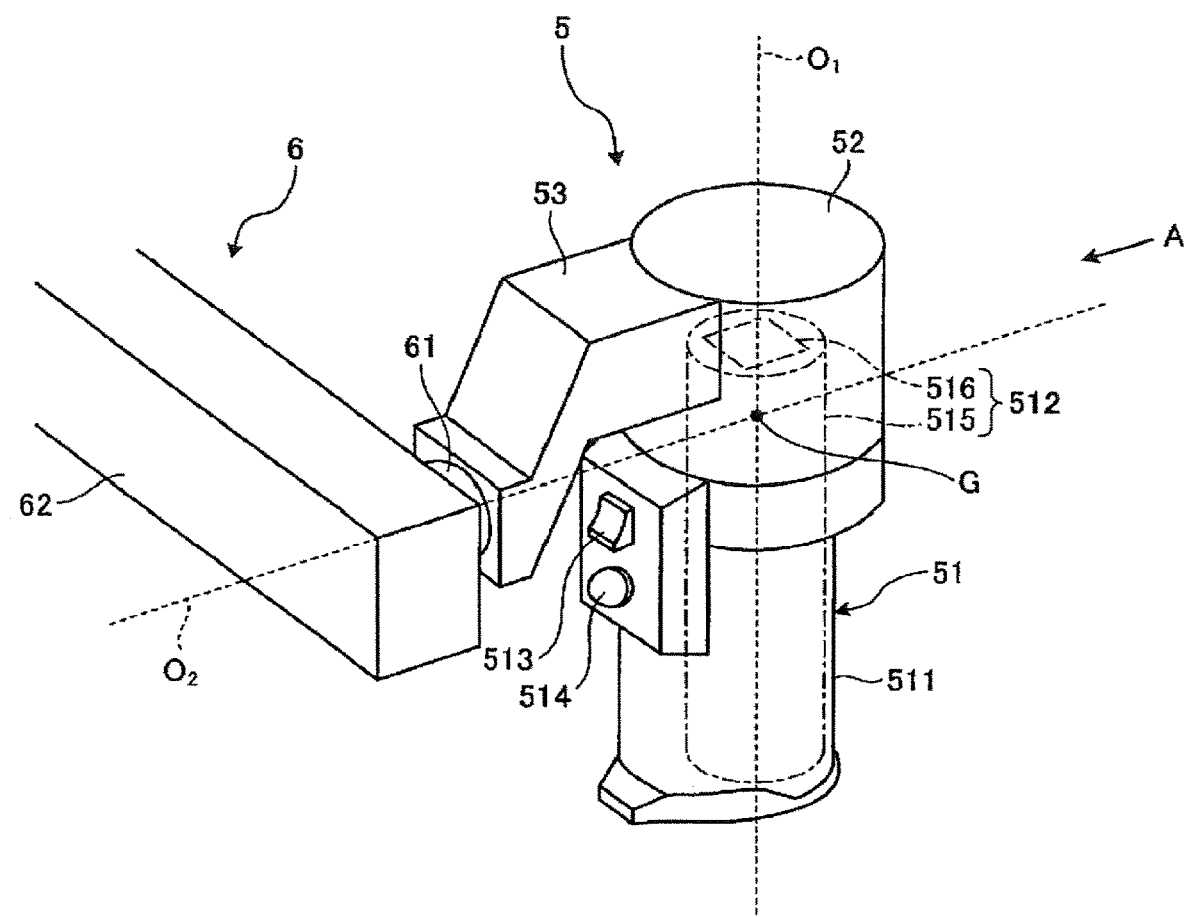
FIG. 2 is an enlarged perspective view showing the configuration of a microscope unit of a medical observation apparatus according to Embodiment 1 of the present disclosure and the vicinity thereof.
Figure 3:
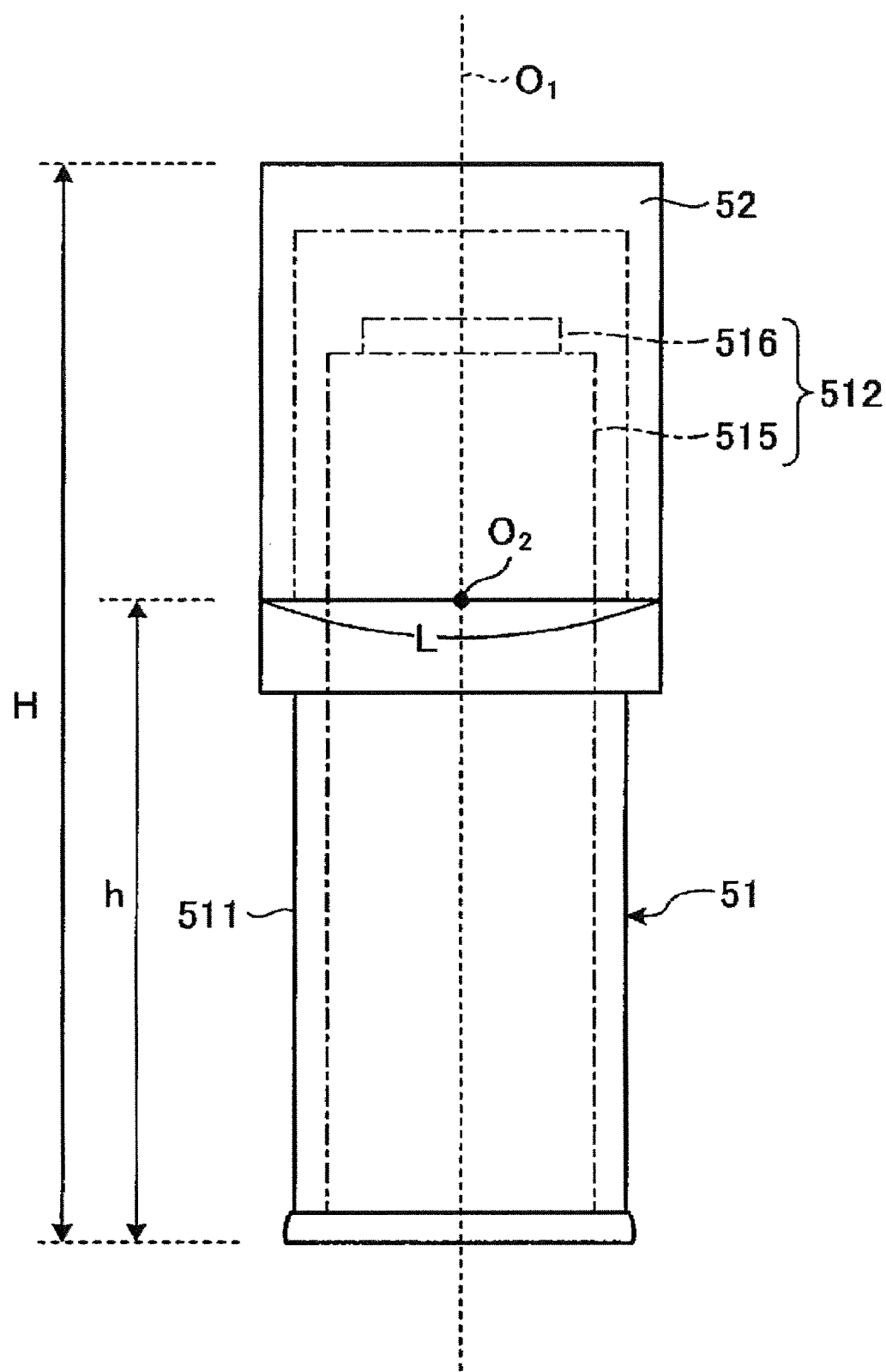
FIG. 3 is a diagram showing the configuration of a main part of the medical observation apparatus according to Embodiment 1 of the present disclosure.

FIG. 2 is an enlarged perspective view showing the configuration of the observation unit 5 and the vicinity thereof. FIG. 3 is a side view as viewed in the direction of arrow A of FIG. 2. The direction of arrow A is a direction orthogonal to a first axis $O_1$ of FIG. 2 and parallel to a second axis $O_2$. The configuration of the observation unit 5 will now be described with reference to FIG. 2 and FIG. 3.

The observation unit 5 includes a microscope unit 51 that images a minute part of an object to be observed with magnification, a first joint unit 52 that holds, on its tip side, the microscope unit 51 in a rotationally movable manner around a first axis $O_1$ in the height direction of the microscope unit 51, and a first arm unit 53 that holds, on its tip side, the first joint unit 52 fixedly.

The microscope unit 51 includes a cylindrical unit 511 having a circular cylindrical shape, an imaging unit 512 that is provided in the hollow portion of the cylindrical unit 511 and captures an image of an object to be observed with magnification, an arm manipulation switch 513 that accepts a manipulation input that permits the movements of the first arm unit 53 and arm units included in the support unit 6 (described later), and a cross lever 514 capable of changing the magnification and the focal distance to the object to be observed in the imaging unit 512. The microscope unit 51 has a columnar shape that is grasped by the user when the microscope unit 51 moves.

The cylindrical unit 511 has a circular cylindrical shape with a diameter smaller than the diameter of the first joint unit 52, and a cover glass that protects the imaging unit 512 is provided on the opening surface at the lower end of the cylindrical unit 511 at which light from an object to be observed is collected (not illustrated). The shape of the cylindrical unit 511 is not limited to a circular cylindrical shape, and may be a polygonal cylindrical shape.

The imaging unit 512 includes an optical system 515 that includes a plurality of lenses arranged such that their optical axes coincide with the first axis $O_1$ and that collects light from an object to be observed and forms an image, and an imaging element 516 that receives light collected by the optical system 515 and photoelectrically converts the light to generate an imaging signal. In FIG. 2, only a cylindrical casing that houses the plurality of lenses included in the optical system 515 is described.

The optical system 515 is capable of changing the magnification of an image of the object to be observed and the focal distance to the object to be observed in accordance with the manipulation of the cross lever 514.

The imaging element 516 is formed using a charge-coupled device (CCD) or a complementary metal oxide semiconductor (CMOS). The imaging element 516 generates and outputs an imaging signal. The imaging signal is transmitted to the control device 3 via a transmission cable provided in the support unit 6.

The imaging unit 512 has entered the interior of the first joint unit 52. In FIG. 3, the optical system 515 and the imaging element 516 installed in the hollow portion of the cylindrical unit 511 and the first joint unit 52 are schematically shown by the alternate long and short dash line. Further, in FIG. 3, the boundary of a portion of the microscope unit 51 that has entered the interior of the first joint unit 52 and rotationally moves relative to the first joint unit 52 together with the cylindrical unit 511 is schematically shown by the alternate long and two short dashes line.

The arm manipulation switch 513 is a push-button switch. The electromagnetic brakes of the first joint unit 52, and a second joint unit 61, a third joint unit 63, a fourth joint unit 65, a fifth joint unit 67, and a sixth joint unit 69 included in the support unit 6 are released while the user keeps the arm manipulation switch 513 pushed. The arm manipulation switch 513 is provided on a side surface on the opposite side to the side surface faced by the user during the manipulation of the microscope unit 51, in other words, on a side surface that is the user's blind spot during the manipulation of the microscope unit 51. The arm manipulation switch 513 constitutes a part of an input unit that accepts an input of an operating instruction to the microscope unit 51.

The cross lever 514 is manipulable along the height direction of the cylindrical unit 511 and the round direction orthogonal to the height direction. The cross lever 514 is provided on the side surface of the cylindrical unit 511 below the arm manipulation switch 513 along the height direction of the cylindrical unit 511. Also the cross lever 514 constitutes a part of the input unit that accepts an input of an operating instruction to the microscope unit 51, similarly to the arm manipulation switch 513.

When the cross lever 514 is manipulated from the state shown in FIG. 2 along the height direction of the cylindrical unit 511, the magnification is changed. When the cross lever 514 is manipulated from the state shown in FIG. 2 along the round direction of the cylindrical unit 511, the focal distance to the object to be observed is changed. For example, when the cross lever 514 is moved upward along the height direction of the cylindrical unit 511, the magnification is increased; and when the cross lever 514 is moved downward along the height direction of the cylindrical unit 511, the magnification is decreased. Further, when the cross lever 514 is moved clockwise along the round direction of the cylindrical unit 511, the focal distance to the object to be observed is increased; and when the cross lever 514 is moved counterclockwise along the round direction of the cylindrical unit 511, the focal distance to the object to be observed is decreased. The assignment of the direction of movement of the cross lever 514 and manipulation is not limited to that described herein.

The first joint unit 52 holds, on its tip side, the microscope unit 51 in a rotationally movable manner, and is held on its root end side by the first arm unit 53 in a state of being fixed to a tip portion of the first arm unit 53. The first joint unit 52 has a circular cylindrical shape, and holds the microscope unit 51 in a rotationally movable manner around the first axis $O_1$ that is the center axis in the height direction of the first joint unit 52.

The first arm unit 53 has a substantially L-shaped configuration extending from an upper end portion of the side surface of the first joint unit 52 in a direction orthogonal to the first axis $O_1$ and parallel to a second axis $O_2$, changing direction obliquely on the way, and extending so as to gradually come close to the second axis $O_2$.

The center of gravity G of the observation unit 5 having the above configuration is located at the point of intersection of the first axis $O_1$ and the second axis $O_2$ as shown in FIG. 2. The second axis $O_2$ passes through the boundary between the cylindrical unit 511 of the microscope unit 51 and the first joint unit 52. When the height of the observation unit 5 is denoted by H and the height from the lower end, which is the light collection side, of the microscope unit 51 to the center of gravity G is denoted by h, the two heights H and h satisfy the relation of $H/2<h\leq2H/3$. In other words, the center of gravity G is located farther from the lower end of the microscope unit 51 than the center of the height in the direction of the first axis $O_1$ and the input unit (the arm manipulation switch 513 and the cross lever 514) are. The center of gravity G may be located near the point of intersection of the first axis $O_1$ and the second axis $O_2$ as long as the relation mentioned above is satisfied, and is preferably located nearer to the lower end of the microscope unit 51 than the point of intersection is. Here, the place near the point of intersection of the first axis $O_1$ and the second axis $O_2$ is, when the diameter of the boundary between the microscope unit 51 and the first joint unit 52 is denoted by L (see FIG. 3 and FIG. 4 described later), a spherical area with a radius of L/2 with center at the point of intersection, preferably a spherical area with a radius of L/4 with center at the point of intersection, and more preferably a spherical area with a radius of L/8 with center at the point of intersection.

In the observation unit 5 having the above configuration, for example, the outer shell of the first joint unit 52 is formed using a material with a relatively large specific gravity, such as brass or a super hard alloy; on the other hand, the outer shell of the cylindrical unit 511 is formed using a material with a relatively small specific gravity, such as aluminum.

Next, the configuration of the support unit 6 is described with reference to FIG. 1. The support unit 6 includes a second joint unit 61, a second arm unit 62, a third joint unit 63, a third arm unit 64, a fourth joint unit 65, a fourth arm unit 66, a fifth joint unit 67, a fifth arm unit 68, and a sixth joint unit 69. The support unit 6 includes three sets each of which is composed of two arm units and a joint unit that links one of the two arm units (the tip side) to the other (the root end side) in a rotationally movable manner. The three sets are specifically (the second arm unit 62, the third joint unit 63, the third arm unit 64), (the third arm unit 64, the fourth joint unit 65, the fourth arm unit 66), and (the fourth arm unit 66, the fifth joint unit 67, the fifth arm unit 68).

The second joint unit 61 holds, on its tip side, the first arm unit 53 in a rotationally movable manner, and is held on its root end side by the second arm unit 62 in a state of being fixed to a tip portion of the second arm unit 62. The second joint unit 61 has a circular cylindrical shape, and holds the first arm unit 53 in a rotationally movable manner around the second axis $O_2$. The second arm unit 62 has a substantially L-shaped configuration, and is linked to the second joint unit 61 in an end portion of the longer line portion of the L shape.

The third joint unit 63 holds, on its tip side, the shorter line portion of the L shape of the second arm unit 62 in a rotationally movable manner, and is held on its root end side by the third arm unit 64 in a state of being fixed to a tip portion of the third arm unit 64. The third joint unit 63 has a circular cylindrical shape, and holds the second arm unit 62 in a rotationally movable manner around a third axis $O_3$ that is an axis orthogonal to the second axis $O_2$ and parallel to the direction in which the second arm unit 62 extends. In the third arm unit 64, the tip side has a circular cylindrical shape, and a hole penetrating in a direction orthogonal to the height direction of the circular cylinder on the tip side is formed on the root end side. The third joint unit 63 is held by the fourth joint unit 65 in a rotationally movable manner via the hole.

The fourth joint unit 65 holds, on its tip side, the third arm unit 64 in a rotationally movable manner, and is held on its root end side by the fourth arm unit 66 in a state of being fixed to the fourth arm unit 66. The fourth joint unit 65 has a circular cylindrical shape, and holds the third arm unit 64 in a rotationally movable manner around a fourth axis $O_4$ that is an axis orthogonal to the third axis $O_3$.

The fifth joint unit 67 holds, on its tip side, the fourth arm unit 66 in a rotationally movable manner, and is, on its root end side, attached fixedly to the fifth arm unit 68. The fifth joint unit 67 has a circular cylindrical shape, and holds the fourth arm unit 66 in a rotationally movable manner around a fifth axis $O_5$ that is an axis parallel to the fourth axis $O_4$. The fifth arm unit 68 is formed of an L-shaped portion and a bar-like portion extending downward from the horizontal line portion of the L shape. The fifth joint unit 67 is, on its root end side, attached to an end portion of the vertical line portion of the L shape of the fifth arm unit 68.

The sixth joint unit 69 holds, on its tip side, the fifth arm unit 68 in a rotationally movable manner, and is, on its root end side, attached fixedly to the upper surface of the base unit 7. The sixth joint unit 69 has a circular cylindrical shape, and holds the fifth arm unit 68 in a rotationally movable manner around a sixth axis $O_6$ that is an axis orthogonal to the fifth axis $O_5$. A root end portion of the bar-like portion of the fifth arm unit 68 is attached to the tip side of the sixth joint unit 69.

The support unit 6 having the configuration described above achieves movements with a total of 6 degrees of freedom, i.e. 3 degrees of freedom of translation and 3 degrees of freedom of rotation, in the microscope unit 51.

The first joint unit 52, the second joint unit 61, the third joint unit 63, the fourth joint unit 65, the fifth joint unit 67, and the sixth joint unit 69 include electromagnetic brakes that prohibit the rotational movements of the microscope unit 51, the first arm unit 53, the second arm unit 62, the third arm unit 64, the fourth arm unit 66, and the fifth arm unit 68, respectively. Each electromagnetic brake is released in a state where the arm manipulation switch 513 provided in the microscope unit 51 is pushed, and the rotational movements of the microscope unit 51, the first arm unit 53, the second arm unit 62, the third arm unit 64, the fourth arm unit 66, and the fifth arm unit 68 are permitted. An air brake may be used in place of the electromagnetic brake.

Figure 4:
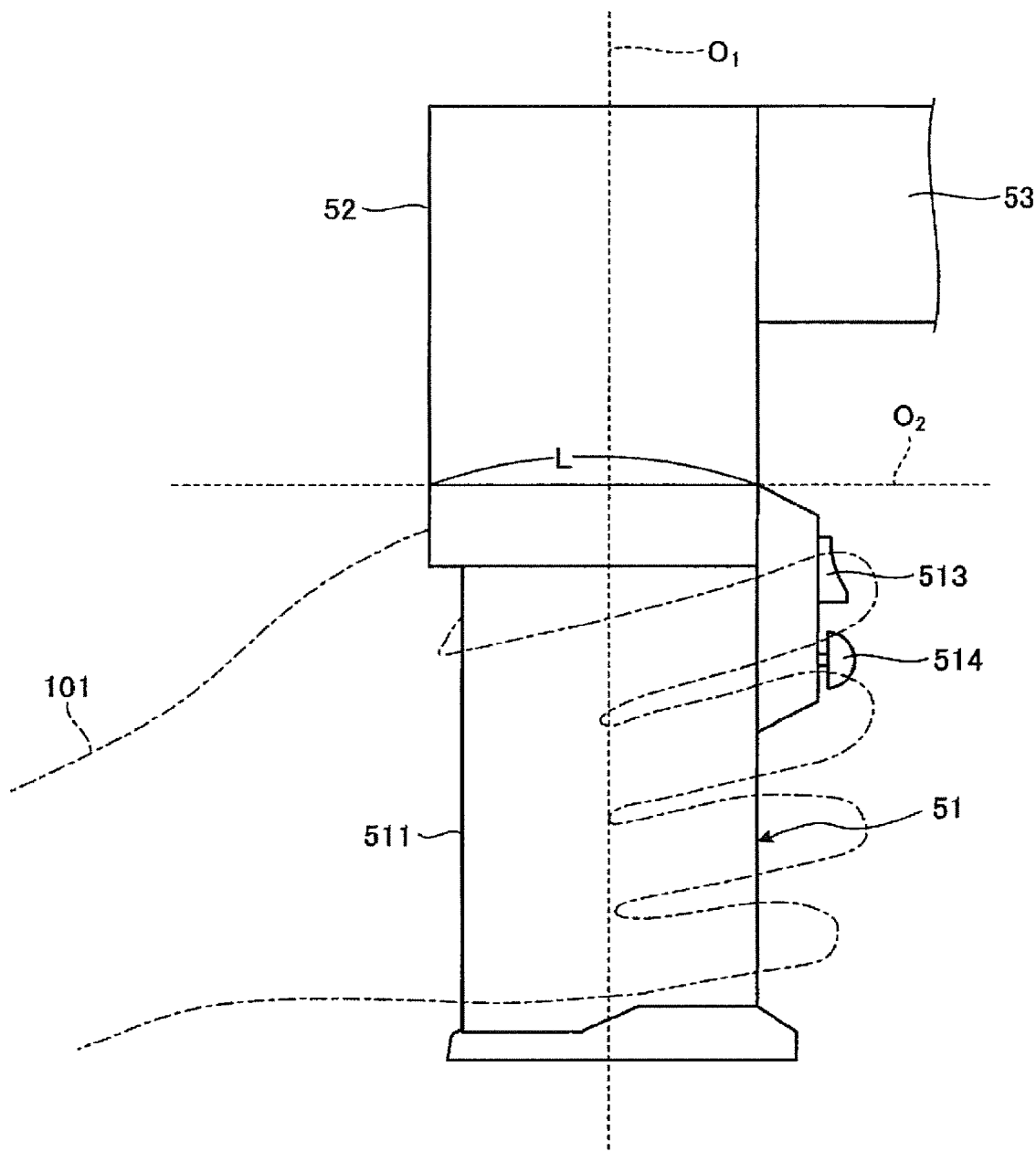
FIG. 4 is a diagram schematically showing a situation where a user manipulates the microscope unit of the medical observation apparatus according to Embodiment 1 of the present disclosure.

FIG. 4 is a diagram schematically showing a situation where a user manipulates the microscope unit 51. The user manipulates the microscope unit 51 while facing, of the side surface of the cylindrical unit 511, a side surface (the left side surface of FIG. 4) on the opposite side to the side surface (the right side surface of FIG. 4) on which the arm manipulation switch 513 and the cross lever 514 are provided. In this event, the user manipulates the support unit 6 while, in a state of grasping the microscope unit 51 with the right hand 101, keeping the arm manipulation switch 513 pushed with the index finger (or the middle finger or the ring finger).

Thus, the user can manipulate the support unit 6 by pushing the arm manipulation switch 513 while naturally grasping the microscope unit 51. In particular, since the position of the center of gravity G of the observation unit 5 is located farther from the lower end of the microscope unit 51 than the center in the height direction of the observation unit 5 is, the height of the cylindrical unit 511 can be ensured sufficiently. The observation unit 5 having such a shape is easy for the user to grasp, and makes it possible to easily perform rotational movement manipulations around the first axis $O_1$ and the second axis $O_2$.

Furthermore, since the arm manipulation switch 513 is provided on, of the side surface of the microscope unit 51, a side surface that is the user's blind spot (a side surface on the opposite side to the side surface faced by the user), the user can perform the manipulation of continuously pushing the arm manipulation switch 513 and the manipulation of pushing and releasing the arm manipulation switch 513 without a sense of incongruity even when the user rotates or tilts the microscope unit 51 in a state of grasping the microscope unit 51 with the hand.

Furthermore, since the user grasps the periphery of the microscope unit 51 with the hand, the user can intuitively recognize the direction of the optical axis of the optical system 515 or the imaging visual field of the microscope unit 51, and can move the microscope unit 51 to a desired position easily.

The configuration of the medical observation system 1 will now be further described.

The control device 3 performs a prescribed signal processing on an imaging signal outputted by the observation apparatus 2 to create image data for display. The control device 3 is configured using a central processing unit (CPU), a read-only memory (ROM), a random access memory (RAM), etc. The control device 3 may be installed in the base unit 7 and integrated with the observation apparatus 2.

The display device 4 receives image data created by the control device 3 from the control device 3, and displays an image corresponding to the image data. The display device 4 like this includes a liquid crystal display panel or an organic electro-luminescence (EL) display panel.

Figure 5:
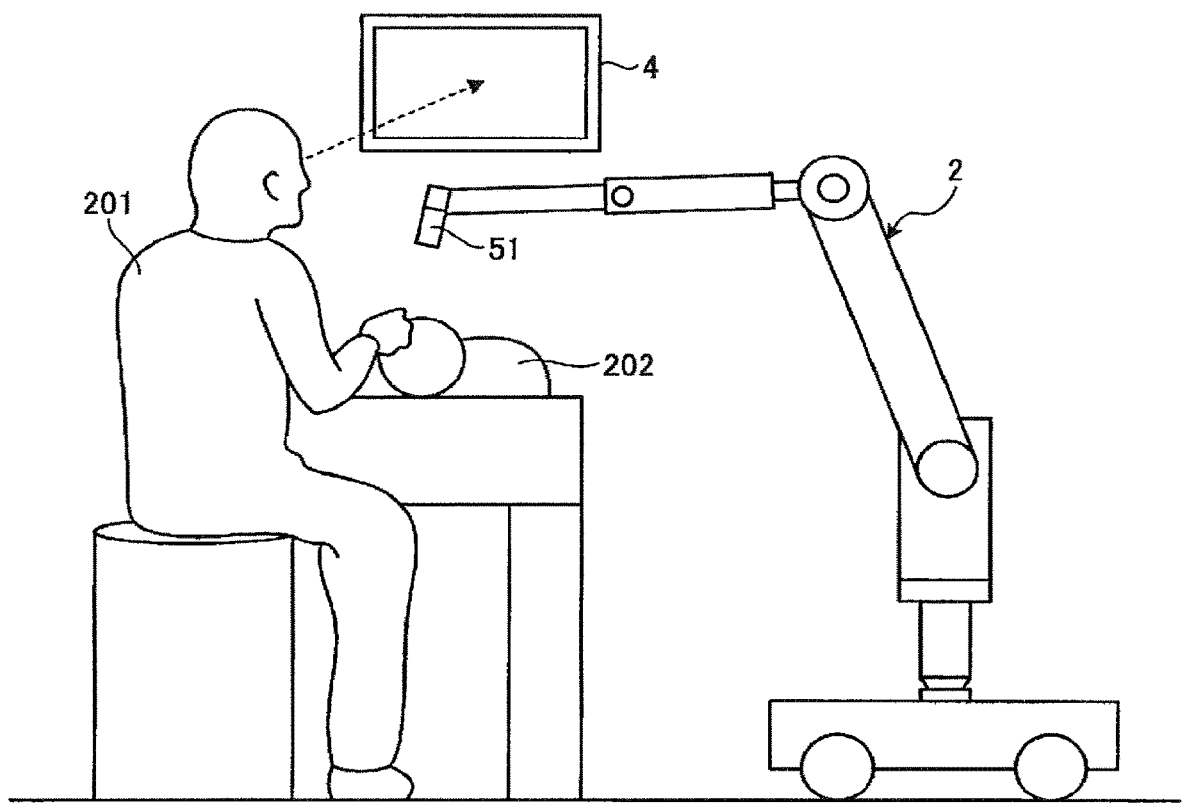
FIG. 5 is a diagram schematically showing a situation of an operation performed using the medical observation system according to Embodiment 1 of the present disclosure.

Next, an overview of an operation performed using the medical observation system 1 having the above configuration is described. FIG. 5 is a diagram schematically showing a situation of an operation using the medical observation system 1. Specifically, FIG. 5 is a diagram schematically showing a situation in which an operator 201 who is the user performs an operation on the head of a patient 202 that is an object to be observed. While visually observing an image displayed by the display device 4, the operator 201 grasps the microscope unit 51 and moves it to a desired position in a state of keeping the arm manipulation switch 513 of the microscope unit 51 pushed and determines the imaging visual field of the microscope unit 51, and then removes the fingers from the arm manipulation switch 513. Thereby, the electromagnetic brake works in the first joint unit 52, the second joint unit 61, the third joint unit 63, the fourth joint unit 65, the fifth joint unit 67, and the sixth joint unit 69, and the imaging visual field of the microscope unit 51 is fixed. After that, the operator 201 performs the adjustment of the magnification and the focal distance to the object to be observed, etc.

In order that the operator 201 can grasp the microscope unit 51 easily and the visual field at the time when the operator 201 views the display device 4 or the surgical site of the patient 202 may not be obstructed, it is preferable that, for example, the outer diameter of the cylindrical unit 511 be approximately 40 to 70 mm, and the height of the observation unit 5 (H of FIG. 3) be approximately 80 to 200 mm.

In Embodiment 1 of the present disclosure described above, the observation unit 5 including the microscope unit 51 that collects light from an object to be observed via one end in the height direction of the microscope unit 51 and captures a magnified image of a minute part of the object to be observed and that has a columnar shape to be grasped by the user during movement, the center of gravity G of which observation unit 5 is located farther from the one end than the center in the height direction is, and the support unit 6 that supports the observation unit 5 in a rotationally movable manner around an axis (the second axis $O_2$) that passes through the center of gravity G or the vicinity of the center of gravity G and is perpendicular to the height direction are provided, and therefore a portion that the user grasps can be sufficiently ensured without increasing the size of the observation unit 5, by shifting the position of the center of gravity G from the center in the height direction of the observation unit 5. Thus, a medical observation apparatus and a medical observation system that are optimal in manipulability and favorable for downsizing can be provided.

Furthermore, in the Embodiment 1, since the distance between the center of gravity G of the observation unit 5 and the lower end of the microscope unit 51 is set larger than ½ of the height of the observation unit and not more than ⅔ of the height of the observation unit, the entire size can be sufficiently reduced while a portion that the user grasps during manipulation is ensured.

Furthermore, in the Embodiment 1, since the user grasps the cylindrical unit 511 of the microscope unit 51 with the hand, the user can intuitively recognize the direction of the optical axis of the optical system 515 or the imaging visual field of the microscope unit 51, and can move the microscope unit 51 to a desired position easily. This is a very advantageous effect as compared to a case like a conventional operating microscope in which a grip provided with a switch for manipulation signal input is apart from the optical axis of the optical system and the optical axis direction cannot be intuitively recognized.

Furthermore, in the Embodiment 1, since the support unit 6 is configured such that a plurality of arm units and joint units are linked, various movements in the observation unit 5 can be achieved by a simpler configuration than a link mechanism like conventional ones.

(Embodiment 2)

Figure 6:
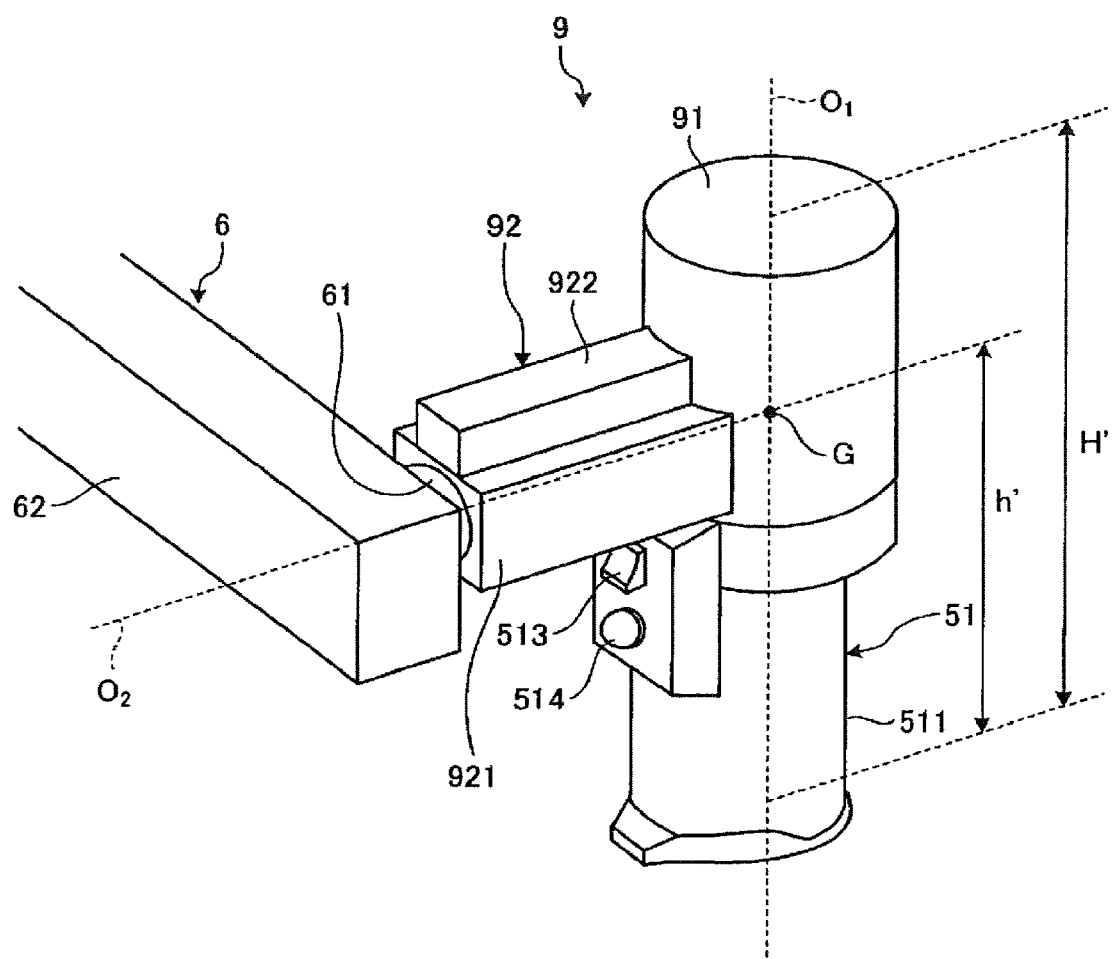
FIG. 6 is a partial cross-sectional view showing the configuration of a main part of a medical observation apparatus according to Embodiment 2 of the present disclosure.

FIG. 6 is an enlarged perspective view showing the configuration of a main part of an observation apparatus included in a medical observation system according to Embodiment 2 of the present disclosure. In the medical observation system according to the Embodiment 2, the configuration of an observation unit 9 is different from the configuration of the observation unit 5 of Embodiment 1. The configuration other than the observation unit 5 is the same as the configuration of the medical observation system 1 described in Embodiment 1.

The observation unit 9 includes the microscope unit 51, a first joint unit 91, and a first arm unit 92. The microscope unit 51 includes the cylindrical unit 511, the imaging unit 512, the arm manipulation switch 513, and the cross lever 514 as described in Embodiment 1 (see FIG. 2 and FIG. 3).

The first joint unit 91 has a circular cylindrical shape; and holds, on its tip side, the microscope unit 51 in a rotationally movable manner around the first axis $O_1$, and is held on its root end side by the first arm unit 92 in a state of being fixed to a tip portion of the first arm unit 92.

The first arm unit 92 has a columnar shape extending from the side surface of the first joint unit 91 along the second axis $O_2$. The first arm unit 92 includes a main body unit 921 in a rectangular parallelepiped shape that is held on its root end side by the second joint unit 61 in a rotationally movable manner around the second axis $O_2$ and a cable housing unit 922 that is provided on, of the side surface of the main body unit 921, a side surface farthest from the lower end of the microscope unit 51 and houses a plurality of transmission cables that transmit signals between the microscope unit 51 and the control device 3. The cable housing unit 922 is formed using a material with a relatively large specific gravity, such as brass or a super hard alloy. In the first arm unit 92, the specific gravity of a first portion located on the lower end side of the microscope unit 51 with respect to a plane that passes through the second axis $O_2$ and is orthogonal to the first axis $O_1$ is smaller than the specific gravity of a second portion located on the opposite side to the first portion and including the cable housing unit 922.

When the height of the observation unit 9 is denoted by H' and the height from the lower end of the microscope unit 51 to the center of gravity G is denoted by h', the two heights H' and h' satisfy the relation of H'/2<h'≤2H'/3. The center of gravity G may be located near the point of intersection of the first axis $O_1$ and the second axis $O_2$ as long as the relation mentioned above is satisfied, and is preferably located nearer to the lower end of the microscope unit 51 than the point of intersection is.

By Embodiment 2 of the present disclosure described above, a medical observation apparatus and a medical observation system that are optimal in manipulability and favorable for downsizing can be provided like in Embodiment 1.

Furthermore, in the Embodiment 2, like in Embodiment 1, a portion that the user grasps during manipulation can be ensured, and the direction of the optical axis of the optical system 515 or the imaging visual field of the microscope unit 51 can be intuitively recognized; thus, the microscope unit 51 can be easily moved to a desired position.

Furthermore, in the Embodiment 2, the cable housing unit 922 made of a material having a larger specific gravity than the main body unit 921 of the first arm unit 92 is provided on a side surface on the side far from the lower end of the microscope unit 51, and thereby the specific gravity of the first portion located on the lower end side of the microscope unit 51 with respect to a plane that passes through the second axis $O_2$ and is orthogonal to the first axis $O_1$ is made smaller than the specific gravity of the second portion located on the opposite side to the first portion and including the cable housing unit 922. Thereby, the center of gravity G of the observation unit 9 can be located farther from the one end of the microscope unit 51 and the input unit than the center of the height in the direction of the first axis $O_1$ of the observation unit 9 is, and the manipulability of the observation unit 5 can be improved. Furthermore, the cable housing unit 922 has both the function of cable housing and the function of a weight, and therefore the waste in design can be eliminated as compared to the case where both functions are provided separately.

(Other Embodiments)

Hereinabove, embodiments of the present disclosure are described; but the present disclosure is not limited to Embodiments 1 and 2 described above. For example, it is also possible to provide two imaging elements in the imaging unit to capture two images having a parallax and use the two images to create and display a three-dimensional image. In this case, the user may wear glasses for three-dimensional images, and can thereby visually observe a three-dimensional image displayed by the display device 4; thus, the user can grasp the surgical site stereoscopically.

The support unit 6 may include at least one set composed of two arm units and a joint unit that links one of the two arm units to the other in a rotationally movable manner.

The manipulation input unit provided in the cylindrical unit 511 is not limited to that described above. For example, a manipulation unit for changing the magnification and a manipulation unit for changing the focal distance to the object to be observed may be provided separately.

Thus, the present disclosure may include various embodiments etc. without departing from the technical idea described in the claims.

Additionally, the present technology may also be configured as below.

(1)

A medical observation apparatus including:

an observation unit including a microscope unit that is configured to collect light from an object to be observed via one end in a height direction of the microscope unit and capture a magnified image of a minute part of the object to be observed and has a columnar shape to be grasped by a user during movement, a center of gravity of which observation unit is located farther from the one end than a center in the height direction is; and a support unit supporting the observation unit in a rotationally movable manner around an axis passing through the center of gravity or a vicinity of the center of gravity and perpendicular to the height direction.

(2)

The medical observation apparatus according to (1), wherein, in the observation unit, a distance between the center of gravity and the one end is larger than ½ of a height of the observation unit and not more than ⅔ of the height of the observation unit.

(3)

The medical observation apparatus according to (1) or (2), wherein the observation unit further includes a first joint unit holding the microscope unit in a rotationally movable manner around a first axis along the height direction, and a first arm unit holding, in its tip portion, the first joint unit and being held in its root end portion by the support unit in a rotationally movable manner around a second axis that is an axis perpendicular to the height direction and orthogonal to the first axis, and the center of gravity is located at a point of intersection of the first axis and the second axis or is located nearer to the one end than the point of intersection is.

(4)

The medical observation apparatus according to (3), wherein, in the first arm unit, a specific gravity of a first portion located on the one end side with respect to a plane passing through the second axis and orthogonal to the first axis is smaller than a specific gravity of a second portion located on an opposite side to the first portion with respect to the plane.

(5)

The medical observation apparatus according to any one of (1) to (4), wherein the observation unit further includes an input unit that is provided on a side surface of the microscope unit, is located nearer to the one end than the center of gravity is, and is configured to accept an input of an operation instruction to the microscope unit.

(6)

The medical observation apparatus according to any one of (1) to (5), wherein the support unit includes at least one set composed of two arm units and a joint unit linking one of the two arm units to the other in a rotationally movable manner.

(7)

A medical observation system including:

the medical observation apparatus according to any one of (1) to (6);

a control device configured to perform signal processing on an imaging signal outputted by the medical observation apparatus to create image data for display; and a display device configured to display an image corresponding to image data created by the control device.

REFERENCE SIGNS LIST 1 medical observation system
2, 9 medical observation apparatus
3 control device
4 display device
5, 9 observation unit
6 support unit
7 base unit
51 microscope unit
52, 91 first joint unit
53, 92 first arm unit
61 second joint unit
62 second arm unit
63 third joint unit
64 third arm unit
65 fourth joint unit
66 fourth arm unit
67 fifth joint unit
68 fifth arm unit
69 sixth joint unit
511 cylindrical unit
512 imaging unit
513 arm manipulation switch
514 cross lever
515 optical system
516 imaging element
921 main body unit
922 cable housing unit

The invention claimed is:

1. A medical observation apparatus comprising:

an observation structure configured to capture an image of an observation object, the observation structure includes at least a columnar shape portion to be grasped by a user during movement, a center of gravity of the observation structure is located in an upper portion of the observation structure; and a support structure supporting the observation structure in a rotationally movable manner at a first joint connected to the observation structure, the first joint rotates around a first axis passing through the center of gravity or a vicinity of the center of gravity and the first axis is different from a longitudinal axis along the columnar shape of the observation structure.

2. The medical observation apparatus according to claim 1, wherein, in the observation structure, a distance between the center of gravity and the one end is larger than ½ of the longitudinal axis along the columnar shape of the observation structure and not more than ⅔ of the longitudinal axis.

3. The medical observation apparatus according to claim 1, wherein the observation structure further includes a second arm that holds, in its tip portion, a second joint and being held in its root end portion by the support structure at the first joint, and the center of gravity is located at a point of intersection of the first axis and the longitudinal axis or is located nearer to the one end than the point of intersection is, and the observation structure further includes a second joint that holds the observation structure in a rotationally movable manner around the longitudinal axis.

4. The medical observation apparatus according to claim 3, wherein, in the second arm, a specific gravity of a first portion located on a side nearer the one end with respect to a plane passing through the first axis and orthogonal to the longitudinal axis is smaller than a specific gravity of a second portion located on an opposite side to the first portion with respect to the plane.

5. The medical observation apparatus according to claim 1, wherein the observation structure further includes an input controller that is provided on a side surface of the observation structure, is located nearer to the one end than the center of gravity is, and accepts an input of an operation instruction to the observation structure.

6. The medical observation apparatus according to claim 1, wherein the support structure includes at least one set composed of two arms and a joint linking one of the two arms to the other in a rotationally movable manner.

7. A medical observation system comprising:
a medical observation apparatus including
- an observation structure configured to capture an image of an observation object, the observation structure includes at least a columnar shape portion a columnar shape to be grasped by a user during movement, a center of gravity of the observation structure is located in an upper portion of the observation structure, and
- a support structure supporting the observation structure in a rotationally movable manner at a first joint connected to the observation structure, the first joint rotates around a first axis passing through the center of gravity or a vicinity of the center of gravity and the first axis is different from a longitudinal axis along the columnar shape of the observation structure;

a control device configured to perform signal processing on an imaging signal outputted by the medical observation apparatus to create image data for display; and a display device configured to display an image corresponding to image data created by the control device.

8. The medical observation apparatus according to claim 1,
wherein the observation structure further includes
a second joint that holds the observation structure in a rotationally movable manner around the longitudinal axis.

9. The medical observation apparatus according to claim 1, wherein materials used in the observation structure are selected to locate the center of gravity in the upper portion of the observation structure.

10. The medical observation apparatus according to claim 1, wherein the microscope includes an optical system with at least one lens that is located above the center of gravity.

11. The medical observation apparatus according to claim 1, wherein, the first axis is perpendicular to the longitudinal axis along the columnar shape of the observation structure.

12. The medical observation apparatus of claim 1, wherein
the observation structure includes a microscope.

13. The medical observation system of claim 7, wherein the observation structure includes a microscope.

* * * * *